US006723714B2

(12) United States Patent  (10) Patent No.: US 6,723,714 B2
Hanna                     (45) Date of Patent:      Apr. 20, 2004

(54) AQUEOUS SOLVENT FOR CORTICOSTEROIDS

(75) Inventor: Calvin Hanna, Little Rock, AR (US)

(73) Assignee: Blansett Pharmacal Co., Inc., Little Rock, AR (US)

( * ) Notice: Subject to any disclaimer, the term of this patent is extended or adjusted under 35 U.S.C. 154(b) by 0 days.

(21) Appl. No.: 09/347,974

(22) Filed: Jul. 6, 1999

(65) Prior Publication Data

US 2002/0013305 A1 Jan. 31, 2002

(51) Int. Cl.$^7$ ............................................... A61K 31/56
(52) U.S. Cl. ...................... 514/177; 514/169; 514/177; 514/179; 514/182; 514/970
(58) Field of Search ................................ 514/179, 182, 514/177, 970

(56) References Cited

U.S. PATENT DOCUMENTS

| | | |
|---|---|---|
| 2,779,707 A | 1/1957 | Jacobson et al. |
| 2,880,130 A | 3/1959 | Johnson et al. |
| 3,422,186 A | 1/1969 | Sasmor |
| 4,213,979 A | 7/1980 | Levine |
| 4,289,764 A * | 9/1981 | Yarrow et al. ............... 424/243 |
| 4,305,936 A | 12/1981 | Klein |
| 5,728,690 A * | 3/1998 | Chen .......................... 514/179 |
| 5,843,930 A * | 12/1998 | Purwar et al. ............... 514/171 |
| 6,093,417 A * | 7/2000 | Petrus ......................... 424/437 |

OTHER PUBLICATIONS

AN 96:3409, Source, Drug Launches, (Apr. 22, 1996, DN 0139550, Trade Name Scalpicin).*
Scalpacin Trademark, United States Trademark Ser. No. 74709103, Filed on Jul. 31, 1995 by Registrant Combe Incorporated.*
Scalpacin Trademark (Cancelled), United States Trademark Ser. No. 74043305, Filed on Mar. 28, 1990 by Registrant Combe Incorporated.*
Zocort HC Trademark (Abandoned), United States Trademark Ser. No. 76103631, Filed on Jun. 12, 2001 by Applicant Qualitest Pharmaceuticals, Incorporated.*
Cortane–B Trademark, United States Trademark Ser. No. 76088583, Filed on Jul. 14, 2000 by Registrant Blansett Pharmacal Co., Incorporated.*
Gupta, Das; The Effect of Some Formulation Adjuncts on the Stability of Hydrocortisone; Drug Development and Industrial Pharmacy, 11(12), pp. 2083–2097 (1985).*
Zocort HC Side Effects, Zocort HC Drug Information, Zocort HC Dosage; www.pharmacyhealth.net/d/zocort–hc–1921.htm.*
Poole, Michael D; Declining Antibiotic Effectiveness in Otitis Media—A Convergence of Data; Ear, Nose, and Throat Journal, Jun. 1998, 77 (6), p. 444.*
Osborne et al.; Skin Penetration Enhancers Cited in the Technical Literature; Pharmaceutical Technology, Nov. 1997, p. 58.*
Adams et al.; "The Effect of Various Amides on the In Vitro Percutaneous Penetration of Hydrocortisone;" School of Pharmacy.
Allen et al.; "Stability of Hydrocortisone in Polyethylene Glycol Ointment Base;" Journal of Pharmaceutical Sciences; Jan. 1974; vol. 63, No. 1; pp. 107–109.
Barry et al.; Solubilization of Hydrocortisone, Dexamethasone, Testosterone and Progesterone by Long–Chain Polyoxyethylene Surfactants; J. Pharm.. Pharmac.; (1976); vol. 28; pp. 210–218.
Bortz et al.; "Composition of Cerumen Lipids;" Journal American Acad Dermatol; Nov. 1990; vol. 23; pp. 845–849.
Gupta, V. Das; Effect of Vehicles and Other Active Ingredients on Stability of Hydrocortisone; Journal of Pharmaceutical Sciences; Mar. 1978; vol. 67, No. 3; pp. 299–302.
Hajratwala et al.; "Effect of Non–Ionic Surfactants on the Dissolution and _ Hydrocortisone;" J. Pharm. Pharmac.; (1976); vol. 28; pp. 934–935 (Complete title is not legible).
Lovgren et al.; "Simultaneous Solubilization of Steroid Hormones I: Estrogens and $C_{21}$ Steroids;" Journal of Pharmaceutical Sciences; Oct. 1978; vol. 67, No. 10; pp. 1419 and 1422 (pp. 1420 and 1421 are missing).
Monder, Carl; "Stability of Corticosteroids in Aqueous Solutions;" Research Institute for Skeletomuscular Diseases of the Hospital for Joint Diseases and Medical Center; Feb. 1968; vol. 82; pp. 318–326.
Robinson et al.; "The Efficacy of Ceruminolytics: Everything Old is New Again;" The Journal of Otolaryngology; (1989); pp. 263.
Robinson et al.; "The Mechanism of Ceruminolysis;" The Journal of Otolaryngology; (1989); pp. 268 and 273 (pp. 269–272 are missing).
Schoenwald et al.; "Relationship Between Steroid Permeability Across Excised Rabbit Cornea and Octanol–Water Partition Coefficients;" Journal of Pharmaceutical Sciences; pp. 786 and 788 (p. 787 is missing).
Shahi et al.; "Effect of Formulation Factors on Penetration of Hydrocortisone Through Mouse Skin;" Journal of Pharmaceutical Sciences; Jun. 1978; vol. 67, No. 6; pp. 789 and 792 (pp. 790 and 791 are missing).
Yalkowsky et al.; "Solubility and Partitioning I: Solubility of Nonelectrolytes in Water," Journal of Pharmaceutical Sciences; Aug. 1980; vol. 69, No. 8; pp. 912–922.

* cited by examiner

Primary Examiner—Sabiha Qazi
(74) Attorney, Agent, or Firm—Clark G. Sullivan, Esq.; King & Spalding LLP

(57) ABSTRACT

A solvent comprising a combination of water and organic solvent(s) capable of dissolving a therapeutically effective amount of medicament(s) not readily soluble in aqueous solvents, said organic solvents including alcohol and glycol, and said medicaments including hydrocortisone.

13 Claims, No Drawings

AQUEOUS SOLVENT FOR CORTICOSTEROIDS

FEDERALLY SPONSORED RESEARCH OR DEVELOPMENT

Not applicable.

BACKGROUND OF THE INVENTION

The invention disclosed herein generally relates to the field of solvents capable of dissolving medicaments. More particularly, it relates to the field of water-containing solvents capable of dissolving medicaments not regularly soluble in aqueous solutions, such as steroids (especially corticosteroids) and antimicrobial phenols (especially chloroxylenol). The present invention is especially suited for dissolving hydrocortisone into a clear solution for topical application.

One application of the present invention is in the field of treatment of ear aches and similar maladies of the ear. One problem to which the present invention is directed is the relative inability of water to dissolve medicaments commonly used to treat such ear maladies, and the relative inability or undesirability of organic solvent solutions for delivery of medicaments for topical applications using certain methods.

The auricle of the ear is covered with a layer of skin that extends part way into the external ear canal. The inner part of the ear canal, including the external surface of the ear drum, is covered with a thin layer of epithelial cells. The outer part of the external ear canal has ceruminous glands which produces a waxy material composed of free fatty acids, other organic compounds, salts and water. This area also contains hair which prevents debris in the immediate environment from entering the ear canal. The epithelial cells of the canal slough off and combine with the waxy organic materials, water, cells, debris and hair to form cerumin, commonly known as ear wax. No bland organic agent or water will dissolve all of the ear wax particles. However, water and organic solvents (and combinations) will loosen and swell the wax.

Excessive water in the ear canal will swell the ear wax, leading to a plugging of the canal, which may thereby become infected. This condition is sometimes called swimmer's ear, or otitis externa. Ear drops containing antimicrobial agents are commonly applied to the external ear canal to abate the infection; other medicaments within the ear drops, such as hydrocortisone, may reduce inflammation, while local anesthetics (such as, for example, pramoxine) reduce pain. Substances such as glycerol, for example, also aid in the removal of excess ear wax.

Ear plugs or wicks made of cloth, plastic or cellulose (collectively "wicks") may be inserted into the ear canal after the ear drop medicaments are applied to the ear canal. These wicks expand and retain the ear drops within the ear canal. For ear drops to expand the wick within several minutes, the ear drops must contain 33% or more water.

Hydrocortisone is approved as 1±0.2% concentration for ear drop pharmaceutical products. Hydrocortisone is nearly insoluble in water (0.028% on a weight volume basis) and glycerol. However, it is soluble to at least 1% in several organic solvents such as propylene glycol, polypropylene glycol diacetate, hexenyl glycol, 2-propanol, ethanol and in pure (glacial) acetic acid. It is also solubalized in non-ionic surfactants (micells and colloids).

Many solutions of hydrocortisone have a relatively short "shelf life," losing efficacy if not used fairly promptly after mixing. The stability of hydrocortisone in solution is relative, since there is a gradual loss of this chemical over time; in many such solutions, hydrocortisone becomes oxidized or otherwise rendered less active (or completely inactive) after a period of days or months in storage at room temperature.

Monder, *Endocrinology* 82(2), 318 (1968), reported that aqueous solutions of hydrocortisone were rapidly oxidized and lost. Short, et al., *J. Pharm. Pharmacology* 61(11), 17825 (1972) studied the cause of the loss of hydrocortisone in solution and Bansal, et al., *J. Pharm. Sci.* 72(9) 1079 (1983) slowed this loss by adding 0.1% fructose. Barry, et al., *J. Pharm. Pharmacology* 28(3), 210 (1976) and Hajratwala, et al., *J. Pharm. Pharmacology* 28(3),934 (1976) reported on surfactants to produce micells of hydrocortisone in water. Lovgren, et al., *J. Pharm. Sci.* 67(10), 1419 (1978), Hagen, et al.,*J. Pharm. Sci.* 72(4), 409 (1983), Gupta, *Drug Development and Industrial Pharmacy* 11(12), 2083097 (1985) reported on the use of surfactants and the loss of hydrocortisone in these solutions.

Due to the low solubility of hydrocortisone in many solvents, such as glycerol and water, the preparation of clear solutions of 1%–2% concentrations of the drug solution is difficult. Co-solvents such as lower molecular weight alcohols, i.e., ethanol, 2-propanol and glycols (propylene glycol, hexenyl glycol) may be added to increase the water content of the solutions. Also, surfactants may be added to form micells in water.

Jacobson, U.S. Pat. No. 2,779,707 disclosed the use of 20% water and 80% hexenyl glycol to prepare 0.8% hydrocortisone acetate to be used for intravenous administration.

U.S. Pat. No. 2,880,130 issued to Johnson in 1959 described the possible use of polyoxyethylene sorbitan monooleate (Tween 80) in amounts of 2–25% for the vehicle to obtain micells in water of 0.2% hydrocortisone. This was to be applied to the eye, ear, nose and throat.

Two Italian patents Rom RO 65,112 and 84,025 reported on the formulation of hydrocortisone and antibiotics in oil for the treatment of otitis externa.

U.S. Pat. No. 3,422,186 issued to Sasmor in 1969 discloses aqueous, viscous solutions of 0.05–0.5% hydrocortisone using (10%) water, propylene glycol, glycerol or polyoxyethylene glycol. These were to be used to dissolve ear wax and to treat ear disease in the human and animal.

A stable, sprayable 0.5% hydrocortisone preparation is disclosed in U. S. Pat. No. 4,213,979 issued to Levine in 1980. Said compound employs polyoxypropylene-(12)-polyoxyethylene-(50)-lanolin, 15% ethanol, 25% propylene glycol to form a film. Moreover, it contains a relatively high ethanol content, limiting its usefulness for topical application (especially to the ear, near the eye).

U.S. Pat. No. 4,289,764 issued to Yarrow et al. in 1981 describes formulations containing 0.025 to 0.4% hydrocortisone in an aqueous propylene glycol (15–50%) solution with citric acid; it discloses dissolving more than 0.1% hydrocortisone in 50:50 v/v water: propylene glycol solution exceed known physical solubility values of hydrocortisone.

U.S. Pat. No. 4,305,936 issued to Klein in 1981 provides for a 0.005 to 2.5% hydrocortisone clear cream formulation containing 1 to 4% by weight of a glycerol ester of fatty acids having 6–22 carbon atoms, 1–3% by weight of the hydrocortisone of a betaine surfactant, and 10–50% of an alkanol co-solvent, preferably ethanol; solutions having such surfactants generally have stability problems, and are not recommended for topical application to the ear. Furthermore, it contains a relatively high ethanol content, limiting its usefulness for topical application (especially to the ear, near the eye).

U.S. Pat. No. 5,728,690 issued to Chen in 1998 discloses a clear non-alcoholic 1–2% hydrocortisone preparation using 15–30% polyethylene glycol, 15–30% propylene glycol, 5–20% glycerol, 3–12.4% sodium diactyl sulfosuccinate, and as much as 20% water to make a liquid or gel product for application to the skin.

U.S. Pat. No. 5,744,166 describes a hydrocortisone composition with aminopolysaccharides; such as, chitosan and chitosan derivatives and polycationic polymers that forms a film when applied dermally.

Purwar, et al., WO 9,639,146 describes an aqueous solution of the antimicrobial ciprofloxacin for the treatment of otitis externa and media. Hydrocortisone is mentioned as a possible ingredient in the ciprofloxacin preparation.

One primary object of the present invention is to provide a clear aqueous solution capable of delivering the optimal allowable amount of medicament(s) for topical application, especially to the ear canal of humans or animals.

Another object of the present invention is to provide a clear aqueous solution containing the optimal amount of hydrocortisone, anti-microbial and anesthetic agents for application as ear drops.

Another object is to provide a solvent capable of dissolving an optimal amount of medicaments not readily soluble in water, yet containing sufficient water to expand a wick.

Another object is to provide a method of making said solution that is easy and relatively inexpensive.

Another object is to provide a stable solution, and one that has a long shelf life.

Another object is to provide a method of using said solution that facilitates delivery of the optimal amount of medicament to the ear.

Other objects will be apparent from a reading of the written description disclosed herein, together with the claims.

SUMMARY OF THE INVENTION

Generally, the solvent and solution disclosed herein (and the methods of making and using same) relate to the formation of solutions using both organic solvents and water. Optimally, said solution will be a clear, aqueous solution capable of delivering a therapeutically effective amount of medicament(s) for topical application, especially to the ear canal; in particular, a preferred embodiment of the solvent and solution disclosed herein will both dissolve a therapeutically effective amount of medicament(s) and have sufficient water content to also promptly swell a wick within the ear canal a sufficient amount to facilitate contact with the ear canal and to thereby facilitate the reduction of ear wax, inflammation, infection and pain.

This invention yields stable, aqueous solutions of hydrocortisone using a bland combination of propylene glycol, water, ethanol or 2-propanol, together with mineral oil and/or propylene glycol diacetate, for the treatment of otitis externa, ear infections, inflammation and/or itching in or around the external ear canal. In addition, medicaments such as an anesthetic (pramoxine, for example) and an antimicrobial (such as chloroxylenol) can be included in the solution. These formulations for external ear treatment are stable in solution; they also have a shelf life exceeding nine months. The ear drop formulations of 1.0% hydrocortisone USP, with at least 33% water, can be used to expand the cellulose, cloth or plastic wick to retain the medication in the ear canal, and to maintain contact between the medicament and the ear canal. This enhances the ceruminolytic efficacy of the solution; the ear wax is broken down, facilitating ease of removal.

DETAILED DESCRIPTION OF THE INVENTION

In most general terms, one primary aspect of the invention disclosed herein is a solvent comprising a combination of water and organic solvent(s) capable of dissolving a therapeutically effective amount of medicament(s) not readily soluble in aqueous solvents. Preferably said water is included in the range of between about 30% (v/v) and about 50% (v/v), to facilitate the wick-expanding facets of the invention. More specifically, said water is included in the range of at least about 33% (v/v).

For the sake of simplicity and to give the claims of this patent application the broadest interpretation and construction possible, the following definitions will apply:

1. The term "alcohol" primarily means alcohols of alkanes having a low molecular weight, such as (for example) the alkanols 2-propanol and ethanol; not usually included are alcohols such as glycol and glycerol.
2. The term "bland" or any similar word means evoking essentially no material adverse reaction after topical application.
3. The term "glycol" primarily means alcohols having at least two alcohol groups, such as (for example) glycol and glycerol.
4. The term "medicaments" means an agent that promotes recovery from an ailment or symptom(s) thereof; such agents may be groups of related substances or compounds (or functional derivatives or equivalents) such as, for example: (a) anti-inflammatory agents like steroids such as hydrocortisone or hydrocortisone derivatives (for example, hydrocortisone hemisuccinate, hydrocortisone sodium phosphate, and hydrocortisone sodium succinate); (b) anti-microbial agents like chloroxylenol, cresyl acetate and phenol; and (c) anesthetic agents like pramoxine and members of the benzoesters or amides group of anesthetics (benzocaine, lidocaine and tetracaine, for example).
5. The phrase "therapeutically effective amount" or similar phrase means the amount necessary to reduce or prevent the symptom or malady stated, implied or inherent in the context of usage.
6. The term "% (v/v)" or a similar phrase means the volume-per-volume percentage concentration of a liquid substance, usually expressed as the number of milliliters (mL) of dissolved in 100 milliliters (mL) of solution.
7. The term "% (w/v)" or a similar phrase means the weight-per-volume percentage concentration of a solid substance, usually expressed as the number of grams of solute dissolved in 100 milliliters of solution.
8. The term "water" may include isotonic saline, and combinations of same with water.

Also for the sake of simplicity, the conjunctive "and" may also be taken to include the disjunctive "or," and vice versa, whenever necessary to give the claims of this patent application the broadest interpretation and construction possible. Likewise, when the plural form is used, it may be taken to include the singular form, and vice versa.

The invention disclosed herein is not limited by construction materials to the extent that such materials satisfy the structural or functional requirements; for example, any materials may be used to make the solvent so long as the solvent allows for the dissolution of a therapeutic amount of medicament while containing sufficient water content for absorption and expansion of a wick. For this reason, the various components of each solvent and solute may include members of specified groups of substances, plus functional derivatives or equivalent substances.

The organic solvent portion of the present invention may be comprised of one or more glycol, especially glycol(s) selected from the group consisting of propylene glycol, glycerol, propylene glycol diacetate, and hexylene glycol, and functional derivatives (or equivalents) and combinations thereof. One of the important characteristics common to each of said members in said group, supporting the inclusion of each member in said particular group, is that glycols (especially propylene glycol) are known to fairly readily dissolve hydrocortisone in sufficient amounts for topical application. Another such common characteristic is that they are bland (i.e., non-irritative) when applied to tissue. Preferably, said glycol may include propylene glycol, and in the range of between about 35% (v/v) and about 65% (v/v). Ideally, the concentration of propylene glycol will not exceed 65%, because it has less solvent properties when cooled, especially to freezing. More particularly, one preferred formulation of the invention provides that said propylene glycol may be included in the range of about 50% (v/v); another preferred formulation of the invention provides that said propylene glycol may be included in the range of about 40% (v/v).

The organic solvent portion of the present invention may be comprised of alcohol, especially the alcohol selected from the group consisting of 2-propanol and ethanol, and functional derivatives (or equivalents) and combinations thereof One of the important characteristics common to each of said members in said group, supporting the inclusion of each member in said particular group, is that is that low molecular weight alcohol are known to readily dissolve hydrocortisone in sufficient amounts (1%) for topical application. Another such common characteristic is that in the event that the hydrocortisone-alcohol solution is cooled to 0° C., said hydrocortisone will remain in said solution. (Hydrocortisone will come out of solution if dissolve in a solution comprised predominantly of glycol.) Preferably, said alcohol may include 2-propanol, and in the range of between about 10% (v/v) and about 80% (v/v). More particularly, one preferred formulation of the invention provides that said 2-propanol may be included in the range of about 16% (v/v); another preferred formulation of the invention provides that said 2-propanol may be included in the range of about 15% (v/v).

It is believed that at least 10% alcohol must be included in the solution containing at least 33% water, to facilitate both the dissolution of hydrocortisone and the expansion of the wick. Assuming the solution contains at least 33% water, ideally the solution should have a minimum concentration in the neighborhood of 10% alcohol, and a maximum concentration of about 55% glycol; similarly, as the concentration of alcohol increases to a maximum in the neighborhood of 30%, the concentration of glycol should decrease to the neighborhood of about 35%. Ideally, the solution should have no more than a total of about 65% combined alcohol and glycol, with alcohol comprising at least 10%, because of its ability to dissolve hydrocortisone when combined with a high enough concentration of water to facilitate expansion of the wick. Moreover, to decrease the danger and discomfort posed by possible contact between the solution and the eye, the concentration of ethanol and/or 2-propanol should not exceed around 30%.

The organic solvent may be comprised of combinations of both alcohol and glycol. For example, a solvent may include 2-propanol in the range of between about 10% (v/v) and about 80% (v/v), and with said glycol including propylene glycol in the range of between about 35% (v/v) and about 65% (v/v). More particularly, in one formulation, said alcohol includes 2-propanol in the range of about 16% (v/v), and said glycol includes propylene glycol in the range of about 50% (v/v); in another formulation, said alcohol includes 2-propanol in the range of about 15% (v/v), and said glycol includes propylene glycol in the range of about 40% (v/v).

The organic solvent may also include propylene glycol acetate, and in the range of between about 0.01% to about 3.0%. As an alternative or additional solvent, mineral oil may be included, and in trace amounts.

The present invention also includes a method of making solvent described above. Said method includes the steps of mixing: (1) glycol selected from the group consisting of propylene glycol, glycerol, propylene glycol diacetate and hexylene glycol, and functional derivatives (or equivalents) and combinations thereof; (2) alcohol selected from the group consisting of 2-propanol and ethanol, and functional derivatives (or equivalents) and combinations thereof; (3) shelf life extender selected from the group consisting of propylene glycol diacetate, mineral oil and vitamin E, and functional derivatives (or equivalents) and combinations thereof; and (4) eventually mixing water (after solute is added to the mixture or (1) through (3) above) in the amount necessary to bring the final solution up to 100%, at least 33% of which is water. In one preferred formulation, said propylene glycol is included in the range of about 50%; said 2-propanol is included in the range of about 16%; and said propylene glycol diacetate is included in the range of about 0.01%. In another preferred formulation, said propylene glycol is included in the range of about 40%; said 2-propanol is included in the range of about 15%; and said mineral oil is included in about trace amounts; this version may also include propylene glycol diacetate in the range specified herein.

Aside from the aforementioned solvents, the present invention may also include a solution of medicament(s) dissolved in solvent, comprising a combination of water and organic solvent(s) capable of dissolving a therapeutically effective amount of medicament(s) not readily soluble in aqueous solvents. An example of the type of medicaments includes anti-inflammatory medicament selected from the group consisting of hydrocortisone, hydrocortisone hemisuccinate, hydrocortisone sodium phosphate, hydrocortisone sodium succinate or other hydrocortisone derivatives, and functional derivatives (or equivalents) and combinations thereof One of the important characteristics common to each of said members in said group, supporting the inclusion of each member in said particular group, is that they are known or believed to have anti-inflammatory effects; hydrocortisone is also approved for topical application in ears in amounts soluble in the invented solvent. Another such common characteristic is that they are relatively stable in the solvent disclosed herein. Preferably, said medicament includes hydrocortisone, and in the range of between about 0.5% to about 2.0%. More particularly, said medicament includes hydrocortisone in the range of about 1.2%.

Another example of said medicament includes anti-microbial medicament selected from the group consisting of chloroxylenol, cresyl acetate and phenol, and functional derivatives (or equivalents) and combinations thereof One of the important characteristics common to each of said members in said group, supporting the inclusion of each member in said particular group, is that they are known or believed to be anti-bacterial and anti-fungal, approved for topical application in ears in amounts soluble in the invented solvent. Preferably, said medicament includes chloroxylenol, and in the range of between about 0.1% to about 0.4%. More particularly, said medicament includes chloroxylenol in the range of about 0.1%.

Another example of said medicament is topical anesthetic medicament selected from the group consisting of pramoxine, benzocaine (and members of the benzocaine-ester group), lidocaine (and members of the lidocaine-amide group), tetracaine, and functional derivatives (or equivalents) and combinations thereof One of the important characteristics common to each of said members in said group, supporting the inclusion of each member in said particular group, is that they are known or believed to have anesthetic effects, and they are approved for topical application in ears in amounts soluble in the invented solvent. Preferably, said medicament includes pramoxine, and in the range of between about 0.5% to about 2.0%. More particularly, said medicament includes pramoxine in the range of about 1.0%.

Another example of said medicament is shelf life extender selected from the group consisting of propylene glycol diacetate, mineral oil and vitamin E, and functional derivatives (or equivalents) and combinations thereof One of the important characteristics common to each of said members in said group, supporting the inclusion of each member in said particular group, is that they are known or believed to extend the shelf life of solutions, thereby extending the efficacy of such solutions. Another such common characteristic is that they help keep hydrocortisone in solution at freezing temperatures. Preferably, said medicament includes propylene glycol diacetate, and in the range of between about 0.01% to about 3.0%. More particularly, said medicament includes propylene glycol diacetate in the range of about 0.01%. As an alternative or substitute shelf life extender said medicament may include mineral oil in the range of its solubility, that is, about trace amounts.

One preferred formulation provides for a solution of medicaments dissolved in solvent, comprising the combination of: (1) solvent comprising propylene glycol in the range of about 50% (v/v), 2-propanol in the range of about 16% (v/v), propylene glycol diacetate in the range of about 0.01% (v/v), and water in the amount necessary to bring the final solution up to 100%; and (2) hydrocortisone in the range of about 1.2% (w/v); and (3) pramoxine hydrochloride in the range of between about 1.0% (w/v); and (4) chloroxylenol in the range of between about 0.1% (w/v). The present invention also includes a method of making a solution described above. Said method includes the steps of:

(a) mixing said non-aqueous solvent components and warming same to about 50° C.;

(b) adding said hydrocortisone and stirring until dissolved;

(c) adding said pramoxine hydrochloride and chloroxylenol, and cooling to about 25° C.; and (d) adding said water to bring the solution to 100% (v/v).

Another preferred formulation provides for a solution of medicaments dissolved in solvent, comprising the combination of: (1) solvent comprising propylene glycol in the range of about 40% (v/v), 2-propanol in the range of about 15% (v/v), mineral oil in about trace amounts, and water in the amount necessary to bring the final solution up to 100%; and (2) hydrocortisone in the range of about 1.2% (w/v); (3) pramoxine hydrochloride in the range of about 1.0% (w/v); and (4) chloroxylenol in the range of about 0.1% (w/v) and/or (5) benzalkonium chloride in the range of about 0.001% (w/v). The present invention also includes a method of making a solution described above. Said method includes the steps of:

(a) mixing said non-aqueous solvent components and warming same to about 50° C.;

(b) adding said hydrocortisone and stirring until dissolved;

(c) adding said pramoxine hydrochloride, and adding said chloroxylenol and/or said benzalkonium chloride, and cooling to about 25° C.; and (d) adding said water to bring the solution to 100% (v/v).

The present invention also includes a method of using medicament solution described herein. Said method may include the steps of: dispensing a therapeutic amount of said solution into an external ear canal; positioning an expandable wick in the external ear canal; and contacting said wick with said solution, in sufficient amount to facilitate expansion of said wick within said canal. In one version of this method of use, said solution is one of the two preferred formulations disclosed above, and said therapeutic amount of said solution is in the range of between about 1 drop and 7 drops.

The following examples are included to illustrate the various formulations useful in this invention and the processes for their preparations.

EXAMPLE I

| Raw Material | |
| --- | --- |
| | % v/v |
| Propylene glycol diacetate, USP | 0.01 |
| Propylene glycol, USP | 50 |
| 2-Propanol, USP | 16 |
| | % w/v |
| Hydrocortisone, USP | 1.2 |
| Pramoxine Hydrochloride, USP | 1.0 |
| Chloroxylenol, USP | 0.1 |
| Water, USP | q.s. to 100% |

Place the propylene glycol diacetate, propylene glycol and 2-propanol in a suitable mixing container equipped with a mixer. Warm the solution to around 50° C. Add hydrocortisone with stirring and when dissolved, add pramoxine hydrochloride and chloroxylenol. Cool to room temperature and bring the solution to 100% with water or isotonic saline.

The solution formulated in Example I remained clear when stored at room temperature for two years. Stability studies on said solution revealed the following: hydrocortisone initially 96.1%; and 94.3% at 90 day shelf life. (Hydrocortisone, USP contains at least 95% hydrocortisone.)

EXAMPLE II

| Raw Material | |
| --- | --- |
| | % v/v |
| Mineral Oil, USP | Trace |
| Propylene glycol, USP | 40 |

-continued

| Raw Material | |
|---|---|
| 2-Propanol, USP | 15 % w/v |
| Hydrocortisone, USP | 1.2 |
| Pramoxine Hydrochloride, USP | 1.0 |
| Chloroxylenol, USP | 0.1 |
| Benzalkonium chloride, USP | |
| Isotonic saline, USP | q.s. to 100% volume |

Prepare as in Example I

The compressed ear plug, Pope Ear Wick Merocel™ is used as an example for hydration and expansion of an ear plug. This wick will expand to maximum size in water at room temperature in less than 0.25 minute; in 80% 2-propanol: 20% water v/v, it will expaned to maximum size in one (1) minute; and in propylene glycol, there is no noticeable expansion. Using the solution formulated in Example I or II, the wick will expand to maximum size in two (2) minutes at room temperature. Also, as the temperature is increased to body temperature, the expansion time is decreased to 30 seconds or less.

Time to Maximum Expansion of Merocel® Pope Ear Wick on Immersion in Example II Solution Initial wick size of 2×3×9 mm; maximum wick size of 10×11×20 mm. Temperature of external ear canal 33° C. [91° F.]; body temperature of 37° C. [98.6° F.].

| Time (minutes) | 2.25 | 1.5 | 0.5 | 0.125 |
|---|---|---|---|---|
| Temp. (° C. [° F.]) | 20 [68] | 26 [79] | 31 [88] | 34 [93] |

7 drop of Example II solution applied to the ears of ten subjects, then 15 seconds elapsed before insertion of ear wick. Removal of ear wick after 30 seconds. Wide expansion sufficient to occlude external ear canal. Expansion of ear wick in room temperature water to maximum in about 15 seconds.

Those skilled in the art who have the benefit of this disclosure will appreciate that it may be used as the creative basis for designing devices or methods similar to those disclosed herein, or to design improvements to the invention disclosed herein; such new or improved creations should be recognized as dependant upon the invention disclosed herein, to the extent of such reliance upon this disclosure.

I claim:

1. A clear stable one phase solution that is non-irritating and resistant to freezing comprising:

a) between about 30% and about 50% water;

b) propylene glycol;

c) 2-propanol or ethanol; and d) hydrocortisone in an amount of about 1.2% USP (w/v), wherein said hydrocortisone is solubilized in said water.

2. The solution of claim 1 wherein said water is present in an amount sufficient to expand an ear wick a therapeutically effective amount when from 1 to 7 drops of the solution are administered to the ear canal.

3. The solution of claim 1 further comprising chloroxylenol in an amount of between about 0.1% (w/v) and about 0.4% (w/v).

4. The solution of claim 1 further comprising chloroxylenol in an amount of about 0.1% (w/v).

5. The solution of claim 1 further comprising pramoxine in an amount of between about 0.5% (w/v) and about 2.0% (w/v).

6. The solution of claim 1 further comprising pramoxine in an amount of about 1.0% (w/v).

7. The solution of claim 1 further comprising chloroxylenol in an amount of between about 0.1% (w/v) and about 0.4% (w/v) and pramoxine in an amount of between about 0.5% (w/v) and about 2.0% (w/v).

8. The solution of claim 1 wherein said propylene glycol is present in an amount of between about 35% (v/v) and about 65% (v/v).

9. The solution of claim 1 wherein said 2-propanol is present in an amount of between about 10% (v/v) and about 80% (v/v).

10. The solution of claim 2 wherein:

a) said 2 propanol is present in an amount of between about 10% (v/v) and about 80% (v/v), b) said propylene glycol is present in an amount of between about 35% (v/v) and about 65% (v/v), and c) said water is present in an amount of between about 30% (v/v) and about 50% (v/v).

11. The solution of claim 1 further comprising propylene glycol diacetate in an amount of between about 0.01% (w/v) and about 0.5% (w/v).

12. The solution of claim 1 further comprising propylene glycol diacetate in an amount of about 0.01% (w/v).

13. The solution of claim 1 further comprising mineral oil.

* * * * *